United States Patent [19]

Lohnes et al.

[11] 4,142,403
[45] Mar. 6, 1979

[54] METHOD AND MEANS FOR TESTING SOILS

[75] Inventors: Robert A. Lohnes; Turgut Demirel, both of Ames, Iowa

[73] Assignee: Iowa State University Research Foundation, Inc., Ames, Iowa

[21] Appl. No.: 842,503

[22] Filed: Oct. 17, 1977

[51] Int. Cl.² .................... G01N 5/04; G01N 25/56
[52] U.S. Cl. ............................................................ 73/76
[58] Field of Search ............................ 73/73, 75, 76, 77

[56] References Cited

U.S. PATENT DOCUMENTS

| | | | |
|---|---|---|---|
| 1,089,826 | 3/1914 | Emerson | 73/76 |
| 2,047,765 | 7/1936 | Brabender | 73/76 |
| 2,709,914 | 6/1955 | Brabender et al. | 73/76 |
| 2,832,215 | 4/1958 | Brabender | 73/76 |
| 3,055,206 | 9/1962 | Watson et al. | 73/76 X |
| 3,074,270 | 1/1963 | Rabb | 73/76 |
| 3,084,537 | 4/1963 | Shipstead et al. | 73/76 X |
| 3,145,562 | 8/1964 | Hamilton et al. | 73/76 |
| 3,463,000 | 8/1969 | Broadwin | 73/76 |
| 3,605,501 | 9/1971 | Chenevert | 73/76 X |
| 3,813,918 | 6/1974 | Moe | 73/76 X |

OTHER PUBLICATIONS

Welch; "Quick-Answer Soil Moisture"; Soil-Test Technical Information; Bulletin C-140-64; Mar. 1964, pp. 1-6.

Primary Examiner—John Petrakes
Attorney, Agent, or Firm—Zarley, McKee, Thomte, Voorhees & Sease

[57] ABSTRACT

An apparatus for testing soils by measuring the rate of moisture loss from soil or sediment samples is disclosed, comprising a test chamber, a fan, a heater-thermostat, a chilled water humidity control device, an automatic balance scale connected to a continuous chart recorder, a shield around the balance pan, and a magnetic damper for the balance pan. The heater-thermostat maintains a constant temperature within the chamber, while the chilled water humidity control device maintains a constant relative humidity. The fan circulates air in the chamber, and the magnetic damper and shield around the balance pan allows the soil sample to be weighed without air currents causing the balance pan to vibrate. The balance scale continually weighs the sample, with the weight being recorded on the chart recorder, thus providing a record of the rate of moisture loss. A bell jar allows the testing to be done under vacuum conditions.

The method of this invention comprises the steps of:
1. Continuously weighing a soil sample as the sample dries.
2. Maintaining a controlled atmosphere of constant temperature and constant relative humidity during the weighing.
3. Continuously recording the weight of the soil sample as it dries.

A variation of this method is disclosed comprising the further step of:
4. Maintaining the soil sample under vacuum during weighing.

11 Claims, 3 Drawing Figures

METHOD AND MEANS FOR TESTING SOILS

BACKGROUND OF THE INVENTION

This invention relates to a method and means for testing soils, and more particularly, to a method and means for testing soils by measuring the rate of moisture loss from soil or sediment samples.

The engineering and agronomic usefulness of a given soil is controlled by the mineralogic composition and fabric or structure of the soil. Present practice requires techniques such as differential thermal analysis, x-ray diffraction or wet chemistry for mineralogical analysis and adsorption isotherm studies, mercury porosimetry, light microscopy or electron microscopy for fabric analysis. All these techniques require expensive instrumentation, considerable time, and highly skilled operators for testing soils. Another problem faced by engineers is the change in physical state of a soil as the moisture content changes. This problem has been answered previously with the use of Atterberg limits tests which are based upon highly empirical and somewhat arbitrary testing procedures. The results of Atterberg limit tests are subject to operator variation and are time-consuming.

SUMMARY OF THE INVENTION

An apparatus for testing soils by measuring the rate of moisture loss from soil or sediment samples is disclosed, comprising a test chamber, a fan, a heater-thermostat, a chilled water humidity control device, an automatic balance scale connected to a continuous chart recorder, a shield around the balance pan, and a magnetic damper for the balance pan. The heater-thermostat is to maintain a constant temperature within the chamber, and the chilled water humidity control device maintains constant relative humidity. The fan circulates air in the chamber, and the magnetic damper and shield around the pan allows the soil sample to be weighed without the air currents causing the balance pan to vibrate. As the sample dries under the controlled environment, it is weighed continuously with the weight recorded on the chart recorder. The rate of moisture loss recorded is used to interpret the fabric and composition of the soil.

To determine mineral content, a sample of standard density and shape is used, while an undisturbed soil sample of standard size and surface area is used to determine fabric as well as composition.

A variation of this device comprises a bell jar to allow weighing of the sample under vacuum.

It is a principal object of this invention to provide a soil testing device for measuring the rate of moisture loss from soil or sediment samples.

A further object of the invention is to provide a soil testing device that is economical to manufacture.

A still further object of the invention is to provide a soil testing device that is relatively simple to operate and not subject to operator variation.

A still further object of the invention is to provide a soil testing device that determines mineralogic composition and/or fabric or structure of soil in a relatively short period of time.

DESCRIPTION OF THE DRAWINGS

This invention consists in the construction, arrangement and combination of the various parts of the device whereby the objects contemplated are obtained as hereinafter more fully set forth, specifically pointed out in the claims, and illustrated in the accompanying drawings, of which:

DESCRIPTION OF THE PREFERRED EMBODIMENT

Water in the pores of solid material may be present in three forms:

1. As capillary water which is held more tightly in smaller pores than in larger pores;
2. As hygroscopic water held as a result of the surface chemical affinity of the solid phase;
3. As free water, which is removable from the solid under a specific set of conditions.

A plot of drying rate versus moisture content of the solid exhibits a constant rate of moisture loss down to a critical moisture content. Below the critical moisture content there is a falling rate period followed by the moisture content coming to equilibrium depending upon temperature, relative humidity, and the nature of the material. The rate of moisture loss during the constant rate period is independent of the nature of the solid and is controlled by air velocity, temperature, humidity and pressure. The shape of the drying curve from the critical moisture content to equilibrium moisture content is controlled by the composition and structure of the solid and the mechanism by which moisture moves within the solid.

In order to use moisture rate loss as an interpretive tool for soil composition and fabric analysis, it is necessary to allow the soil to dry out under a controlled environment so that any observed variations in the drying rate of soils is the result of variations in soil properties, not variables such as temperature, humidity and air currents.

Figure 1:
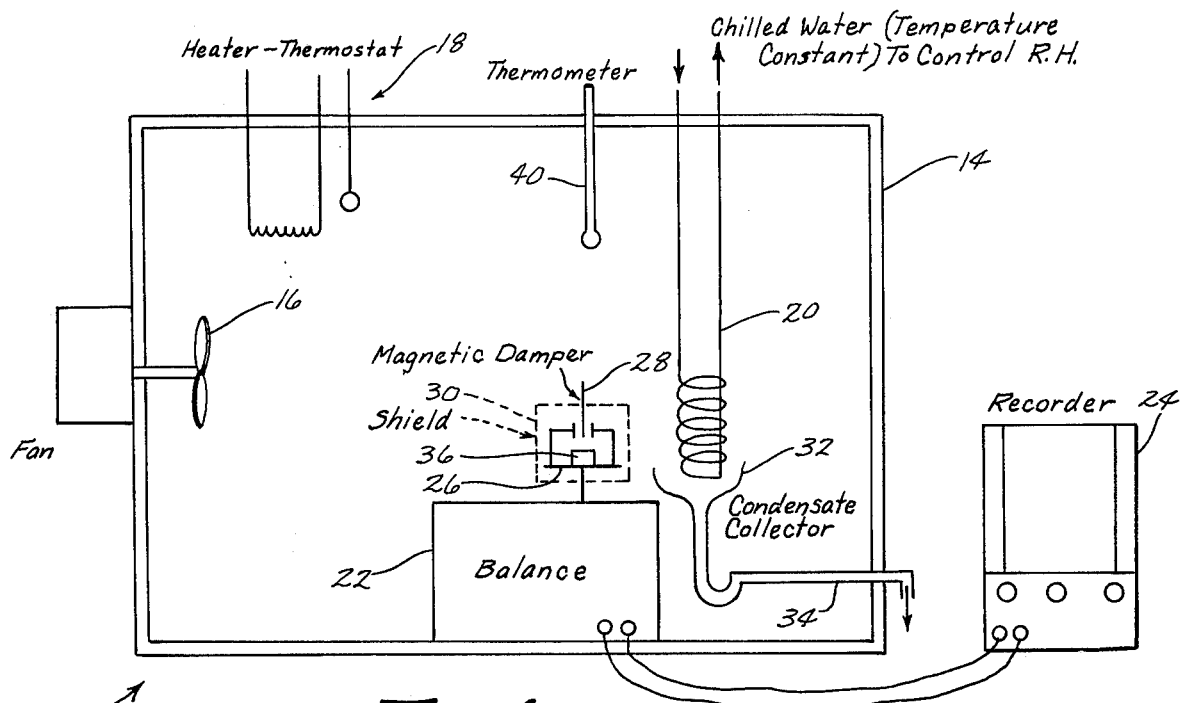
FIG. 1 is a schematic view of the invention.
Figure 3:
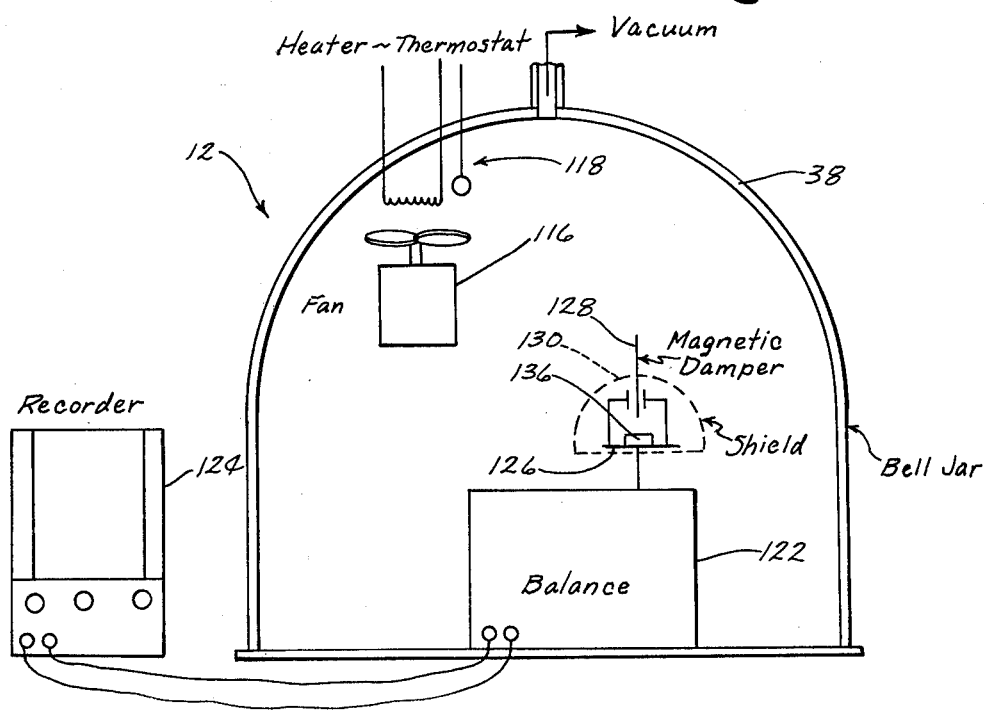
FIG. 3 is a schematic view of an alternate embodiment of the device.

To achieve these ends, the moisture evaporation rate meter 10 shown in FIG. 1, and the alternate embodiment, moisture evaporation rate meter 12, shown in FIG. 3, are utilized. Meter 10 provides weighing under a controlled atmosphere, while meter 12 allows weighing under vacuum.

Moisture evaporation rate meter 10 comprises a test chamber 14, fan 16, heater-thermostat 18, chilled water humidity control device 20, automatic balance scale 22, and chart recorder 24. Recorder 24 is electrically connected to balance scale 22 to automatically and continuously record the readings of balance scale 22. Balance pan 26 contains a magnetic damper 28 and a shield 30, as shown in FIG. 1. The condensate from humidity control device 20 is collected by collector element 32 and removed from test chamber 14 by drain pipe 34.

Heater-thermostat 18 maintains a constant temperature within chamber 14, while humidity control device 20 maintains a constant relative humidity. Fan 16 circulates the air in the chamber, while magnetic damper 28 and shield 30 around the balance pan 26 allows the soil sample 36 to be weighed without the air currents causing the balance pan 26 to vibrate. Thermometer 40 provides a visual indication of chamber temperature.

Figure 2:
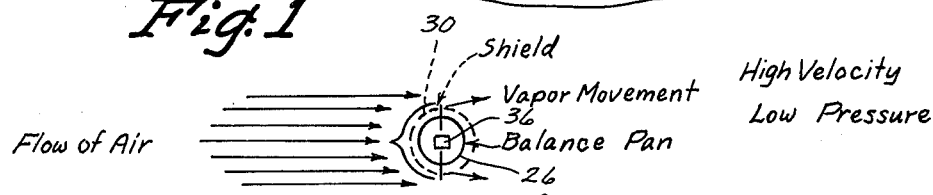
FIG. 2 is a top view of the air flow around the balance pan.

FIG. 2 illustrates the air flow around balance pan 26 and shield 30.

In order to determine mineral content of a soil, samples will be compacted to a standard density and shape. For all soils tested, the initial constant rate period of the drying curve will be identical for identical drying conditions. The critical moisture content and the falling rate periods, on the other hand, will vary from soil to soil, depending upon the composition of the soil. After the sample is compacted to a standard density and shape, the sample is weighed continuously, and as the sample dries under the controlled environment of meter 10, the weight is continuously recorded on the chart recorder 24. The rate of moisture loss thus recorded can be used to interpret the mineral composition of the soil. Undisturbed soil samples can also be placed in the evaporation rate meter 10. As with the disturbed samples, i.e., compacted to a standard density and shape, there will be a standardization of sample size and surface area. In this case, the critical moisture content and falling rate periods will reflect the fabric as well as the composition of the soils which are tested. The actual interpretation of the rate of evaporation curves will depend upon empirical correlations of soil composition and fabric with the evaporation behavior.

To continuously weigh a sample under vacuum, moisture evaporation rate meter 12, shown in FIG. 3, is utilized. Meter 12 comprises bell jar 38, heater-thermostat 118, fan 116, balance scale 122, magnetic damper 128, shield 136, and continuous chart recorder 124. A vacuum is maintained within bell jar 38, and heater-thermostat 118 maintains a constant temperature within bell jar 38. Fan 116 circulates the air in bell jar 38, and magnetic damper 128 and shield 136 around balance pan 126 allow the soil sample to be weighed without the air currents causing the balance pan to vibrate.

Again, the various components of the system are utilized to provide a controlled atmosphere for the measurement of evaporation rates. The sample is weighed continuously, and as the sample dries under the controlled conditions, the weight is continuously recorded on chart recorder 124. The data produced, and the interpretation of the data, will be the same as with meter 10.

The vacuum evaporation rate meter 12 will enable the operator to run the tests rapidly, since under vacuum, overall evaporation rates are considerably higher than those obtainable when surrounding atmosphere is under pressure. In addition, the equilibrium moisture contents in the vacuum evaporation meter will tend toward zero and thus will enable the operator to determine evaporation rates at moisture zones which are critical for some minerals such as allophanes and montmorillonites.

Thus, a method and means is shown for measuring soil drying rates to be used as an interpretive tool for determining soil structure and composition. As can be seen, this invention accomplishes at least all of its stated objectives.

We claim:

1. A device for measuring the rate of evaporation in soil, comprising:
    a testing chamber means;
    means to selectively maintain a constant temperature within said chamber means;
    means to maintain constant relative humidity within said chamber means;
    means to circulate air within said chamber means;
    scale means to continuously weigh a soil sample within said chamber means; and
    recording means operationally connected to said scale means to continuously record the weight of said soil sample.

2. The device of claim 1 wherein said scale means comprises a balance pan having a shield element therearound and a magnetic damping means to insulate said pan from vibration due to the circulation of air.

3. The device of claim 1 wherein said testing chamber means comprises a vacuum container means to maintain the interior of said chamber means under a vacuum.

4. The device of claim 3 wherein said vacuum container means comprises a bell jar.

5. The device of claim 1 wherein said recording means comprises a visual chart recorder.

6. A method for measuring the rate of moisture loss from a soil sample to determine soil composition and structure, comprising
    maintaining a controlled atmosphere of constant temperature and constant relative humidity within a testing area;
    continuously weighing a soil sample within said area as said sample dries, and
    recording the weight of said sample.

7. The method of claim 6 wherein said soil sample is compacted to a predetermined density and shape before said weighing.

8. The method of claim 6 wherein said soil sample is shaped to a predetermined size and surface area before said weighing.

9. The method of claim 6 wherein maintaining said controlled atmosphere comprises maintaining a vacuum within said area.

10. The method of claim 6 wherein said recording is continuous and permanent.

11. The method of claim 10 wherein said recording is chart recording.

* * * * *